(12) United States Patent
Josten et al.

(10) Patent No.: US 9,085,746 B2
(45) Date of Patent: Jul. 21, 2015

(54) PROCESS FOR OBTAINING OLEOCHEMICALS WITH REDUCED CONTENT OF BY-PRODUCTS

(75) Inventors: Horst Josten, Düsseldorf (DE); Ewelina Sobierska, Düsseldorf (DE); Adrian Chan, Düsseldorf (DE); Truc Tran Anh, Düsseldorf (DE)

(73) Assignee: Cognis IP Management GmbH, Duesseldorf (DE)

( * ) Notice: Subject to any disclaimer, the term of this patent is extended or adjusted under 35 U.S.C. 154(b) by 374 days.

(21) Appl. No.: 13/470,277

(22) Filed: May 12, 2012

(65) Prior Publication Data

US 2012/0289726 A1 Nov. 15, 2012

Related U.S. Application Data

(60) Provisional application No. 61/485,807, filed on May 13, 2011.

(51) Int. Cl.
| | |
|---|---|
| *C11B 7/00* | (2006.01) |
| *C11B 3/14* | (2006.01) |
| *C07C 29/149* | (2006.01) |
| *C11C 3/00* | (2006.01) |
| *C11C 3/12* | (2006.01) |
| *C07C 67/03* | (2006.01) |

(52) U.S. Cl.
CPC ............... *C11B 3/14* (2013.01); *C07C 29/149* (2013.01); *C11C 3/003* (2013.01); *C11C 3/12* (2013.01); *C07C 67/03* (2013.01)

(58) Field of Classification Search
None
See application file for complete search history.

(56) References Cited

U.S. PATENT DOCUMENTS

| | | | | |
|---|---|---|---|---|
| 4,089,880 | A * | 5/1978 | Sullivan | 554/176 |
| 4,599,143 | A * | 7/1986 | Stage | 203/6 |
| 4,608,202 | A | 8/1986 | Lepper et al. | |
| 4,810,330 | A * | 3/1989 | Stage | 203/4 |
| 4,976,892 | A | 12/1990 | Jeromin et al. | |
| 2008/0051599 | A1 * | 2/2008 | Adami et al. | 560/129 |

FOREIGN PATENT DOCUMENTS

| | | |
|---|---|---|
| DE | 4321837 | 1/1995 |
| EP | 0127104 | 3/1987 |
| EP | 0332971 | 9/1993 |
| EP | 1092703 | 1/2004 |
| GB | 533847 | * 2/1941 |

* cited by examiner

*Primary Examiner* — Yate K Cutliff
(74) *Attorney, Agent, or Firm* — Servilla Whitney LLC

(57) ABSTRACT

Processes for obtaining fatty acids with reduced content of by-products, wherein unrefined fats or oils are subjected to steam stripping in a counter-current column to produce a bottom fraction of de-acidified fats or oils, a first distillate consisting mainly of fatty acids and glycerides, and a second distillate comprising fatty acids and essentially all unwanted ketones, aldehydes and phenols, and the bottom fraction containing the de-acidified fats or oils is combined with the first distillate containing fatty acids and glycerides.

12 Claims, 2 Drawing Sheets

PROCESS FOR OBTAINING OLEOCHEMICALS WITH REDUCED CONTENT OF BY-PRODUCTS

CROSS-REFERENCE TO RELATED APPLICATIONS

This application claims priority under 35 U.S.C. §119(e) to U.S. Provisional Application No. 61/485,807, filed May 13, 2011, the disclosure of which is incorporated herein by reference in its entirety.

FIELD OF THE INVENTION

The present invention is related to the area of oleochemicals and refers to an improved process for obtaining fatty acids, fatty acid alkyl esters and fatty alcohols with reduced content of ketones, aldehydes and phenols and their hydrogenation products.

BACKGROUND

State of the art technologies for the manufacturing of fatty alcohols from vegetable oils and fats are high or low pressure transesterification with methanol and suitable catalysts followed by high pressure hydrogenation. While high pressure transesterification has the advantage that unrefined oils and waste fat streams with high amount of free fatty acids can be used as raw materials, one major disadvantage is that impurities contained in the crude raw materials, like aldehydes, ketones and phenols are converted in the transesterification and hydrogenation steps into chemical species, which are difficult to separate from the fatty alcohols and reduce the quality of the final products. On the other hand, for low pressure transesterification with e.g. sodium methylate as catalyst the final product qualities are better due to the use of refined oils as feed materials, but higher raw material prices need to be accepted.

According to the state of the art many different processes for processing oils and fats of different qualities are known. For example, EP 0127104 B1 (Cognis) discloses a process for making fatty acid esters of short-chain, aliphatic alcohols by catalytic transesterification of natural fats and/or oils containing free fatty acids (oil phase) with the corresponding alcohols, the oil phase is subjected to preliminary esterification with the alcohols in the presence of acidic esterification catalysts at temperatures no higher than 120° C. and under pressures of less than 5 bar and in the presence of a liquid entraining agent substantially immiscible with the oil phase, after which the reaction product is separated into an entraining agent phase containing the acidic catalyst and water of reaction and the treated oil phase. Subsequently, the oil phase is then subjected to transesterification while the acidic catalyst-containing entraining agent phase is returned, after at least partial drying, to the preliminary esterification stage. By this process, fats and/or oils with acid numbers of up to 60 can be processed in the preliminary esterification stage to give an oil phase having a low acid number.

EP 1092703 B1 (Cognis) teaches the preparation of fatty acid methyl esters having an acid number of less than 0.1 comprises subjecting a fatty acid glyceride, having an acid number of 5 to 20, with methanol in a ratio of 0.4 to 0.7% w/v to a two stage esterification process comprising a first high-pressure and a second low-pressure esterification Unfortunately, none of the processes according to the state of the art provide a simple and economic method to convert cheap unrefined oils into high quality fatty acids.

One or more embodiments of the invention provide cheap—which means in particular unrefined—fats and oils as raw materials available for producing purified, high quality fatty acids serving as intermediates for fatty acid alkyl esters and—as the following stage of derivatisation—fatty alcohols also showing an improved quality. In particular, it is the essence of the proposed new process to substantially remove unwanted by-products such as ketones, aldehydes and phenols and to collect them in a fraction of waste material, said fraction representing less than 1% b.w. calculated on the total amount of raw material subjected to the purification process. In the context of the present invention the term "to substantially remove" shall have the meaning to remove at least 80, in particular at least 90 and more preferably about 95% of unwanted ketones, aldehydes and phenols from the unrefined oils.

DETAILED DESCRIPTION

Figure 1:
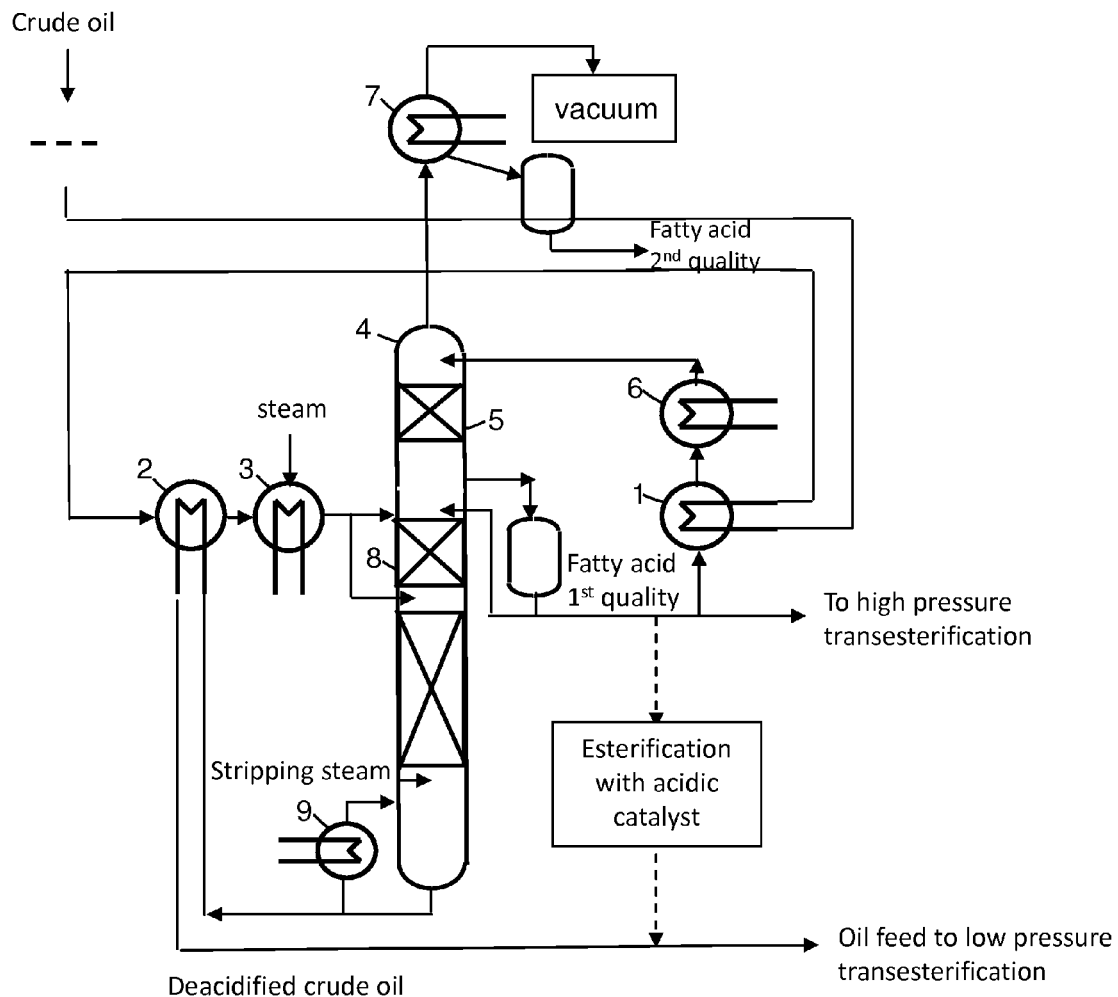
FIG. 1 shows a flow sheet of a process for the reduction of impurities from unrefined oils in accordance with one or more embodiments of the invention.

A first aspect of the present invention relates to a process for obtaining fatty acids with reduced content of by-products, wherein
(a) unrefined fats or oils are subjected to steam stripping in a counter-current column to produce
  (i) a bottom fraction of de-acidified fats or oils,
  (ii) a first distillate consisting mainly of fatty acids and glycerides, and
  (iii) a second distillate comprising fatty acids and essentially all unwanted ketones, aldehydes and phenols; and
(b) said bottom fraction (i) containing the de-acidified fats or oils and said first distillate (ii) containing fatty acids and glycerides are combined.

A second aspect of the present invention refers to a process for obtaining fatty acid alkyl esters with reduced content of by-products, wherein
(a) unrefined fats or oils are subjected to steam stripping in a counter-current column to produce
  (i) a bottom fraction of de-acidified fats or oils,
  (ii) a first distillate consisting mainly of fatty acids and glycerides, and
  (iii) a second distillate comprising fatty acids and essentially all unwanted ketones, aldehydes and phenols; and
(b) said bottom fraction (i) containing the de-acidified fats or oils and said first distillate (ii) containing fatty acids and glycerides are combined; and
(c) the combined fractions thus obtained are subjected to transesterification with lower $C_1$-$C_4$ alcohols, specifically methanol or ethanol.

A third aspect of the present invention is directed to a process for obtaining fatty alcohols with reduced content of by-products, wherein
(a) unrefined fats or oils are subjected to steam stripping in a counter-current column to produce
  (i) a bottom fraction of de-acidified fats or oils,
  (ii) a first distillate consisting mainly of fatty acids and glycerides, and
  (iii) a second distillate comprising fatty acids and essentially all unwanted ketones, aldehydes and phenols; and (b) said bottom fraction (i) containing the de-acidified fats or oils and said first distillate (ii) containing fatty acids and glycerides are combined;

(c) the combined fractions thus obtained are subjected to transesterification with lower $C_1$-$C_4$ alcohols; and (d) the transesterification products thus obtained are subjected to hydrogenation.

Accordingly, one or more embodiments of the invention remove unwanted by-products from the oils and fats in order to achieve a purified fraction of fatty material that leads also to improved qualities in the esterification to form fatty acid alkyl esters and subsequently in the hydrogenation to obtain fatty alcohols.

While processes according to the state of the art already disclose the de-acidification of crude fats and oils showing acid values of about 10 and higher by steam-stripping in order to produce a de-acidified bottom product and a stream of fatty acids which is taken off at the side or the top of the column, embodiments of the present invention subject said stream of free fatty acids to a fractionated condensation in order to recover a first distillate of fatty acids from the column vapours which is poor in unwanted by-products and a second distillate taken off from the top of column, containing more than 90% b.w. of all ketones, aldehydes and phenols which have been present in the unrefined fats or oils. Since the top fraction typically represents only 1, in particular about 0.5% b.w. of the total mass of the distillation products (bottom product plus side streams) the amount of waste material compared to other processes is much smaller, which provides an additional economic advantage over the state of the art. Also, the first fatty acid distillate taken off as the side stream shows a seriously reduced content of by-products and thus represents also a valuable product, which can be combined with the bottom fraction of the de-acidified oils for transesterification or can be applied for other purposes.

De-Acidification of the Unrefined Oils

The processes according to one or more embodiments of the present invention can be applied to all kinds of vegetable oils, in particularly those oils showing an acid value typically of 1 to 20, but also higher. Examples of suitable oils—without limitation—are palm oil, palm kernel oil, coconut oil, olive oil, sunflower oil, saflor oil, soy oil, line oil, rape oil, fish oil, lard oil, tallow and their mixtures.

The combined de-acidification and separation of impurities from crude fats or oils is specifically done under vacuum in a counter-current column with stripping steam as shown in FIG. 1. Typically, the crude oil is pre-heated by economizers (1, 2) and pre-heater (3) and fed to the top of the column (4). While trickling down the column free fatty acids and other low boiling impurities like aldehydes, ketones and phenols are stripped from the oil with stripping steam, which is introduced at the column bottom. The stripped off fatty acids and impurities are condensed from the stripping steam in two steps while the de-acidified oil is taken from the column as bottom product.

The column internals can either be structured or dumped packing or trays depending on the solids or gum content of the crude oil. For embodiments involving coconut oil or palm kernel oil structured packing may be used due to low pressure drop. For oils with higher solids/gum content umbrella bubble cap trays are preferred due to lower pressure drop than for other tray types. The height of the packing can be about 3 to about 8, specifically about 4 to about 6 m. The number of trays may be about 6 to about 18, specifically about 8 to about 14. Partial condensation of the fatty acid vapours is typically performed by a partial condenser ("dephlegmator") or more specifically by a direct condensation in a packing (5) with recirculation loop and external plate cooler (6). Vapours leaving the partial condenser are condensed in the second condenser (7). An additional feature of the invention is to install an additional packing (8) above the feed and run the column with a small reflux—about 1 to about 10% of the distillate— of the first distillate in order to reduce the amount of glycerides in the fatty acid distillate. In this case an additional reboiler (9) is required to provide the heat of vaporization for the reflux stream.

The de-acidification column may be operated at a vacuum of about 2 to about 20, specifically about 5 to about 10 mbar. The crude oil feed may be heated to about 225 to about 280, specifically about 245 to about 260° C. The stripping steam rate may be adjusted to about 1 to about 5% w/w, while it is preferred to adjust the rate to about 1 to about 2% w/w of the crude oil feed rate. The resulting acid values of the de-acidified oils and fats are typically between about 0.02 and about 1 and specifically between about 0.1 and about 0.5, the resulting water content between about 0.01 and about 0.1, specifically between about 0.01 to about 0.03%. Adjusting the condenser temperature to about 70 to about 100, and preferably about 80° C., lower boiling impurities (aldehydes, ketones, phenols), which are stripped off from the crude oil, are enriched in the second condensate and thus can be minimized in the main fatty acid distillate. The second condensate can either be discarded as waste or be used as a low fatty acid quality for technical applications.

Depending on the process conditions the first distillate of the de-acidification column contains mainly—which means about 50 to about 99% b.w. —fatty acids, the rest being glycerides. This stream can either directly be routed to high pressure transesterification or esterified and subsequently routed to a low or high pressure transesterification together with the bottom product from the column.

Figure 2:
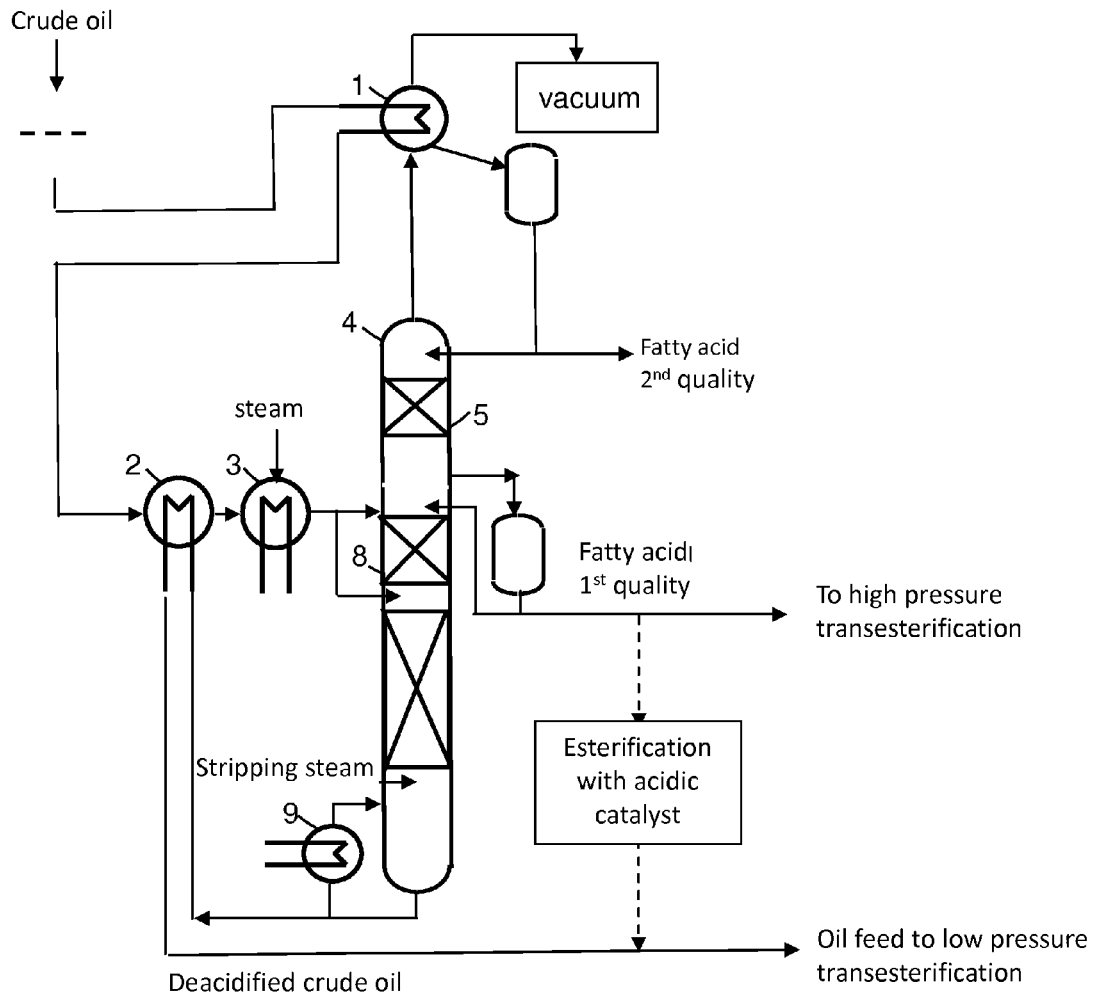
FIG. 2 shows a flow sheet of an alternative procedure for the reduction of impurities from unrefined oils in accordance with one or more embodiments of the invention.

To further improve the separation of the unwanted impurities, an alternative procedure is to replace the partial condensation shown in FIG. 1 by a fractionation in a packed section in the top of the column (5) with refluxing and fractionating at least a part of the second quality fatty acid as shown in FIG. 2. Doing this the split of the low-boilers between the fatty acid qualities can substantially be improved.

Transesterification and Hydrogenation

The reaction mixture leaving the transesterification step is then hydrogenated and the resulting fatty alcohol mixture is improved in quality compared to the processing of unrefined oils without the described de-acidification procedure. These processes represent major operations in technical industry and are well known for one skilled in the art so that additional explanations are not necessary. As an example reference is made to EP 0332971 B1 (Henkel) referring to the transesterification of fatty acid lower alkyl esters and DE 4321837 A1 (Henkel) disclosing the hydrogenation of methyl esters to fatty alcohols which is conducted in two fixed-bed reactors.

EXAMPLES

Example 1

Raw coconut oil with an acid value of 12 had the following content of low-boiling impurities:

| Impurity | Content [ppm] |
| --- | --- |
| $C_7$ Ketone | 29 |
| $C_9$ Ketone | 71 |
| $C_{11}$ Ketone | 581 |
| $C_{13}$ Ketone | 19 |
| Phenol | 214 |

The oil was pre-heated to 260° C. via a pre-heater and pumped at a flow rate of 200 kg/hr to the top of a column with an internal diameter of 130 mm packed with 4.6 m of a structured packing with a specific surface of 350 m²/m³. The column was run at a top pressure of 10 mbar. Stripping steam was introduced into the bottom of the column at a flow rate of 2.0 kg/h. The condenser of the column was adjusted to 80° C., a second condenser to 40° C. The de-acidified oil had an acid value of 0.14, ketone and phenol contents were reduced to below detection limit. In the first condenser a fatty acid stream of 10.6 kg/h was condensed having an acid value of 182.4 and a glyceride content of 16%. Contents of low-boiling impurities were:

| Impurity | Content [ppm] |
| --- | --- |
| $C_7$ Ketone | 17 |
| $C_9$ Ketone | 70 |
| $C_{11}$ Ketone | 1,971 |
| $C_{13}$ Ketone | 343 |
| Phenol | 240 |

In the second condenser 0.6 kg/hr were condensed, having an acid value of 284 and a glyceride content of 0.5%. Contents of low boiling impurities were:

| Impurity | Content [ppm] |
| --- | --- |
| $C_7$ Ketone | 0 |
| $C_9$ Ketone | 310 |
| $C_{11}$ Ketone | 30,423 |
| $C_{13}$ Ketone | 351 |
| Phenol | 10,478 |

The resulting ketone and phenol contents of a mixture of the de-acidified oil and the recovered fatty acids prior to a transesterification according to the current invention would be:

| Impurity | Content [ppm] |
| --- | --- |
| $C_7$ Ketone | 0.9 |
| $C_9$ Ketone | 3.7 |
| $C_{11}$ Ketone | 104.8 |
| $C_{13}$ Ketone | 18.2 |
| Phenol | 12.8 |

Compared to the feed material an overall reduction of total ketones by 82% and of phenol by 94% was achieved.

Example 2

Raw coconut oil with an acid value of 9.5 had the following content of low-boiling impurities:

| Impurity | Content [ppm] |
| --- | --- |
| $C_7$ Ketone | 33 |
| $C_9$ Ketone | 73 |
| $C_{11}$ Ketone | 570 |
| $C_{13}$ Ketone | 14 |
| Phenol | 237 |

The oil was pre-heated to 245° C. via a pre-heater and feeded at a flow rate of 200 kg/h to the third packing of a column as shown in FIG. 2 with an internal diameter of 130 mm equipped with three sections of a structured packing with a specific surface of 500 m²/m³, each of the packages having a height of 1.25 m. The column was run at a top pressure of 10 mbar. Stripping steam was introduced into the bottom of the column at a flow rate of 2.0 kg/h. The condenser of the column was adjusted to 40° C. The condensed second quality fatty acid was split into 0.2 kg, which were taken as top-cut and 14.7 kg reflux, which were fed back to the column top. Below the first packing a first quality was taken off as a liquid side stream, which was split into 8.4 kg takeoff and 10.1 kg reflux. The de-acidified oil had an acid value of 0.16; ketone and phenol content were reduced below detection limit. The first fatty acid quality had an acid value of 195 and a glyceride content of 3%. Contents of low-boiling impurities were:

| Impurity | Content [ppm] |
| --- | --- |
| $C_7$ Ketone | 0.8 |
| $C_9$ Ketone | 6.6 |
| $C_{11}$ Ketone | 193 |
| $C_{13}$ Ketone | 15.1 |
| Phenol | 12.8 |

The second fatty acid quality had an acid value of 288 and a glyceride content of 0.1%. Contents of low-boiling impurities were:

| Impurity | Content [ppm] |
| --- | --- |
| $C_7$ Ketone | 35.5 |
| $C_9$ Ketone | 498 |
| $C_{11}$ Ketone | 33,270 |
| $C_{13}$ Ketone | 3,330 |
| Phenol | 893 |

The resulting ketone and phenol contents of a mixture of the de-acidified oil and the recovered fatty acids prior to a transesterification according to the current invention would be:

| Impurity | Content [ppm] |
| --- | --- |
| $C_7$ Ketone | 0.003 |
| $C_9$ Ketone | 0.3 |
| $C_{11}$ Ketone | 8.1 |
| $C_{13}$ Ketone | 0.6 |
| Phenol | 0.54 |

Overall a reduction of total ketones by 98.7% and of phenol by 99.7% was achieved.

The invention claimed is:

1. A process for obtaining fatty acids with reduced content of by-products by subjecting unrefined fats or oils to purification, wherein
   (a) steam stripping the unrefined fats or oils under vacuum in a counter-current column, wherein the unrefined oils or fats are fed to a top of the column while the stripping steam is led counter-currently from a bottom of the column, to produce
      (i) a bottom fraction of de-acidified fats or oils,
      (ii) a first distillate consisting essentially of fatty acids and glycerides, and
      (iii) a second distillate comprising fatty acids and ketones, aldehydes and phenols; and
   (b) combining said bottom fraction (i) containing the de-acidified fats or oils and said first distillate (ii) containing fatty acids and glycerides to provide a combined fraction;
   and wherein the unrefined oils or fats are selected from the group consisting of palm oil, palm kernel oil, coconut oil, olive oil, sunflower oil, sailor oil, soy oil, line oil, rape oil, fish oil, lard oil, tallow and their mixtures.

2. A process for obtaining fatty acid alkyl esters with reduced content of by-products by subjecting unrefined fats or oils to purification, the process comprising
   (a) steam stripping unrefined fats or oils under vacuum in a counter-current column, wherein the unrefined oils or fats are fed to a top of the column while the stripping steam is led counter-currently from a bottom of the column, to produce
      (i) a bottom fraction of de-acidified fats or oils,
      (ii) a first distillate consisting essentially of fatty acids and glycerides, and
      (iii) a second distillate comprising fatty acids and essentially all unwanted ketones, aldehydes and phenols; and
   (b) combining said bottom fraction (i) containing the de-acidified fats or oils and said first distillate (ii) containing fatty acids and glycerides to provide a combined fraction; and
   (c) transesterifying said combined fraction with lower $C_1$-$C_4$ alcohols; and wherein the unrefined oils or fats are selected from the group consisting of palm oil, palm kernel oil, coconut oil, olive oil, sunflower oil, sailor oil, soy oil, line oil, rape oil, fish oil, lard oil, tallow and their mixtures.

3. A process for obtaining fatty alcohols with reduced content of by-products by subjecting unrefined fats or oils to purification, the process comprising
   (a) steam stripping unrefined fats or oils under vacuum in a counter-current column, wherein the unrefined oils or fats are fed to a top of the column while the stripping steam is led counter-currently from a bottom of the column, to produce
      (i) a bottom fraction of de-acidified fats or oils,
      (ii) a first distillate consisting essentially of fatty acids and glycerides, and
      (iii) a second distillate comprising fatty acids and essentially all unwanted ketones, aldehydes and phenols; and
   (b) combining said bottom fraction (i) containing the de-acidified fats or oils and said first distillate (ii) containing fatty acids and glycerides to provide a combined fraction;
   (c) transesterifying said combined fraction with lower $C_1$-$C_4$ alcohols to provide transesterification products; and
   (d) hydrogenating said transesterification products thus obtained are subjected to hydrogenation
and wherein the unrefined oils or fats are selected from the group consisting of palm oil, palm kernel oil, coconut oil, olive oil, sunflower oil, sailor oil, soy oil, line oil, rape oil, fish oil, lard oil, tallow and their mixtures.

4. Process according to claim 1, wherein oils of fats showing an acid value of from 1 to 20 are subjected to purification.

5. Process according to claim 1, wherein the counter-current column contains packings.

6. Process according to claim 1, wherein the column contains packings above a feed to the column.

7. Process according to claim 1, wherein the column is run with a small reflux of the first distillate.

8. Process according to claim 1, wherein the column is operated at a reduced pressure of 2 to 20 mbar.

9. Process according to claim 1, wherein the column is operated at temperatures of 225 to 280° C.

10. Process according to claim 1, wherein one or more condensers are operated at temperatures of 70 to 100° C.

11. Process according to claim 1, wherein at least a part of the second distillate is refluxed and fractionated in a packing section in a top of the column.

12. Process according to claim 1, wherein the second distillate is no more than 1% b.w. of the total mass of the bottom fraction, first distillate and second distillate.

* * * * *